United States Patent [19]

Haluska

[11] Patent Number: 5,002,052
[45] Date of Patent: Mar. 26, 1991

[54] SYSTEM AND METHOD FOR DETECTION AND TREATMENT OF VENTRICULAR ARRHYTHMIAS

[75] Inventor: Edward A. Haluska, Angleton, Tex.

[73] Assignee: Intermedics, Inc., Angleton, Tex.

[21] Appl. No.: 237,720

[22] Filed: Aug. 29, 1988

[51] Int. Cl.$^5$ .............................................. A61N 1/00
[52] U.S. Cl. ............................................. 128/419 PG
[58] Field of Search .......... 128/419 P, 419 D, 419 PG

[56] References Cited

U.S. PATENT DOCUMENTS

| | | | |
|---|---|---|---|
| 4,475,551 | 10/1984 | Langer et al. ................... | 128/419 D |
| 4,750,494 | 6/1988 | King .............................. | 128/419 PG |
| 4,790,317 | 12/1988 | Davies ........................... | 128/419 PG |
| 4,830,006 | 5/1989 | Haluska et al. ................ | 128/419 PG |

*Primary Examiner*—Francis Jaworski
*Assistant Examiner*—George Manuel
*Attorney, Agent, or Firm*—John R. Merkling

[57] ABSTRACT

A method for detecting and treating ventricular tachyrhythmias of a patient's heart includes the steps of selectively dividing the heart rate continuum into regions including at least two classes of tachycardia, contiguous to each other and of progressively higher heart rate ranges, the lowest and highest of the tachycardia classes being bounded respectively by a sinus rate region and a fibrillation region of the continuum; selectively adjusting the boundaries between the tachycardia classes and between the lowest and highest of those classes and the respective sinus rate and fibrillation regions, to correspondingly adjust the rate ranges of the classes; selectively detecting cardiac events anywhere within the continuum and distinguishing between normal and abnormal tachycardias among the detected events; selectively treating a detected abnormal tachycardia with any of a multiplicity of therapy regimens of differing degrees of aggressiveness, toward terminating the detected tachycardia; with the improvement of preventing, during selectively detecting cardiac events, the classification of a ventricular response to atrial fibrillation as a reentrant ventricular tachycardia.

10 Claims, 3 Drawing Sheets

SYSTEM AND METHOD FOR DETECTION AND TREATMENT OF VENTRICULAR ARRHYTHMIAS

CROSS-REFERENCE TO RELATED APPLICATIONS

This application is related to co-pending U.S. Pat. No. 4,830,006 filed June 17, 1986, in the names of Haluska et al. (referred to herein as the "Haluska et al"09 application), and assigned to the same assignee as the present invention.

BACKGROUND OF THE INVENTION

The present invention pertains to implantable cardiac stimulators for detection and treatment of ventricular arrhythmias, and corresponding methods therefor, and more particularly to a system and method for reliably detecting reentrant ventricular tachycardias.

Although atrial tachycardia (AT) and atrial fibrillation (AF) are generally hemodynamically tolerated because the atria contribute relatively little to cardiac output, special treatment may be necessitated in cases where the patient is symptomatic or at high risk in events of AT or AF. With ventricular tachycardia (VT), cardiac output may be significantly diminished because the ventricles, the main pumping chambers, are only partially filled between the rapid contractions. Moreover, there is a high risk that the VT may accelerate into ventricular fibrillation (VF), spontaneously or in response to treatment of the VT. In that event, there is an instantaneous cessation of cardiac output as a result of the ineffectual quivering of the ventricles. Unless cardiac output is restored almost immediately, tissue begins to die for lack of oxygenated blood, and death will occur within minutes.

It is a principal object of the present invention to provide improved systems and techniques for detecting ventricular tachycardia, and for distinguishing such arrhythmias from normal high rates, to assure rapid delivery of appropriate therapy.

In the Haluska et al application, an implantable cardiac stimulator is disclosed that integrates the functions of bradycardia and anti-tachycardia pacing-type therapies, and cardioversion and defibrillation shock-type therapies, to provide a coordinated approach to the management and treatment of ventricular arrhythmias, including VT and VF. A significant aspect of that approach is to provide flexible sequencing among the therapies, with appropriate regard to hemodynamic tolerance (or intolerance) of the patient to the detected arrhythmia, and sophisticated detection of arrhythmias together with means for distinguishing those episodes for which treatment is required (such as reentrant tachycardias) from those which are not associated with cardiac or other disease (such as exercise-generated sinus tachycardias). The coordinated approach of that invention further takes into account and deals effectively with the risk of acceleration of a tachycardia, as well as with considerations of longevity of the power source for an implantable device, and of patient acceptance of the device.

According to the invention disclosed in the Haluska et al application, a multiplicity of hierarchical detection algorithms and hierarchical therapeutic modalities are selectively available to the physician and applicable to detect and treat classes of ventricular tachycardia according to their respective positions in the heart rate continuum, and thus according to hemodynamic tolerance or intolerance of the patient to the tachycardia, with backup capabilities of defibrillation and bradycardia pacing for cardiac arrhythmias at the respective higher and lower regions of the rate continuum. Aggressiveness of the therapy is increased with elapsed time and with increasing abnormal heart rate. The physician is provided with complete control over the aggressiveness of the therapy for a particular patient and tachyrhythmia, utilizing a hierarchical approach to treatment. The methodology employed in developing the hierarchy is such that physician control is imparted over a wide variety of possible therapy regimens ranging from the basic to the highly complex, with relatively simple programming of the device.

In an embodiment of that invention, the cardiac stimulator permits selective partitioning of the heart rate continuum into a plurality of contiguous tachycardia classes of progressively higher rate ranges, the lowest and highest of these classes being bounded respectively by regions of the continuum denoting sinus rate and fibrillation. Each of the rate ranges and the latter regions may be arbitrarily designated by the physician, as may be necessary to meet the particular needs of the patient's disorder and the flexibility of the therapy regimens to be prescribed. The stimulator includes a hierarchical detection system for detecting cardiac episodes indicative of arrhythmia and for distinguishing between normal and abnormal tachycardias among the detected episodes, using criteria of greater or lesser stringency depending on the location of the episode in the rate continuum. In response to detection of an arrhythmia, the stimulator will automatically deliver one or more therapies according to the physician's exact prescription (based on various factors including, for example, specific patient data, arrhythmia rate, episode longevity and acceleration or deceleration). The available therapies include bradycardia pacing, anti-tachycardia pacing, cardioverting shocks, and defibrillating shocks, which may be delivered separately or in any combination (according to the physician's prescription) to treat the detected arrhythmia, with an ascending order of aggressiveness of the therapy according to the degree of hemodynamic intolerance of the arrhythmia.

In the invention disclosed in the Haluska et al application, the hierarchy of algorithms developed for detecting arrhythmias in the various rate ranges may be assigned to make the criteria progressively less stringent for detecting episodes in progressively higher rate ranges, so that the detection criteria are relaxed with increasing hemodynamic intolerance of the arrhythmia.

It has been found that in certain circumstances, the detection algorithms may incorrectly detect a particular ventricular response as a reentrant ventricular tachycardia. In such instance, the improper detection would result in the delivery of the selected therapy or sequence of therapies to terminate the VT, when in fact the application of such therapy is unnecessary and undesirable.

Accordingly, it is object of the present invention to provide detection criteria and algorithms which avoid the misclassification of ventricular activity as a reentrant VT.

SUMMARY OF THE INVENTION

Briefly, according to the present invention, an algorithm is added to those ventricular tachycardia algorithms employed in an implantable automatic cardioverter and/or defibrillator such as the device described in the Haluska et al application, to preclude the erroneous detection of a ventricular response to atrial fibrillation as a reentrant ventricular tachycardia, and thereby to prevent the improper delivery of therapy. The algorithms are derived from criteria indicative of cardiac events demonstrating high rate, sudden onset, rate stability and/or sustained high rate. In the case of an algorithm in which detection is based on high rate and sudden onset and rate stability, or sustained high rate, the ventricular response to atrial fibrillation may produce an apparent sustained high rate of the ventricles which deceives the sustained high rate criterion and allows such an algorithm to incorrectly classify that response as a reentrant ventricular tachycardia.

According to the invention, this problem is eliminated by use of another detection algorithm which adds rate stability to the sustained high rate portion of the possibly misclassifying algorithm.

BRIEF DESCRIPTION OF THE DRAWINGS

The above and still further objects, features and advantages of the present invention will become apparent from the following detailed description of a presently preferred embodiment, taken in conjunction with the accompanying drawings, in which.

DETAILED DESCRIPTION OF A PREFERRED EMBODIMENT

Figure 1A:
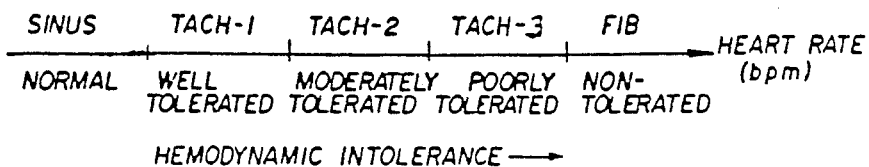
FIGS. 1a and 1b are diagrams illustrating partitioning of the heart rate continuum into arrhythmia classes.

The present invention is used in the context and environment of the invention disclosed in the Haluska et al application, which is incorporated herein by reference. For the sake of convenience to the reader, however, a relevant portion of that disclosure will be presented in summary fashion but with sufficient detail for an understanding of the present invention. Referring to FIG. 1a, the heart rate continuum is partitioned into a multiplicity of regions defining contiguous, successive heart rate ranges consistent respectively with sinus rhythm (SINUS), progressively higher rate ranges associated with VT (TACH-1, TACH-2, and TACH-3) and to rates associated with VF (FIB). In partitioning the rate spectrum, the rate ranges are representative of degrees of hemodynamic tolerance of the patient to the respective cardiac rates, i.e., in the example of FIG. 1a heart rates in the SINUS region are normal, the ascending order of the three VT regions depicts well tolerated, moderately tolerated, and poorly tolerated classes of tachycardia, and rates in the FIB region are not tolerated at all.

Figure 1B:
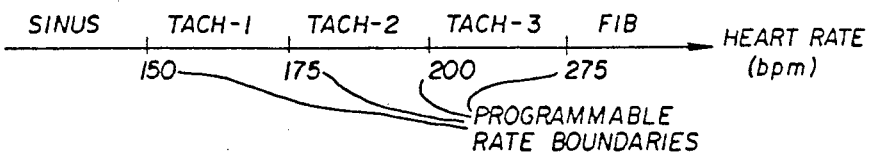

By way of example, the lower and upper boundaries of the TACH-1 region are set at 150 and 175 bpm, and of the TACH-3 region at 200 and 275 bpm, thereby defining the rate range of the TACH-2 region as well as the upper boundary of the SINUS region and the lower boundary of the FIB region, as illustrated in FIG. 1b. Each boundary rate is programmable by the physician, based on the data of the particular patient, and the selected rates are stored in computer memory associated with the central microprocessor of the cardiac stimulator.

In addition, the physician may prescribe any of a plurality of basic therapies for treatment of the arrhythmias, specify the fine structure of each of the therapies, designate the sequence in which the therapies will be delivered in response to a detected arrhythmia in any region of the rate continuum, and select the algorithms for detecting arrhythmias in each region. For example, any of four basic therapies may be designated to treat detected events in each of the arrhythmia classes TACH-1, TACH-2, TACH-3, and FIB. The number and complexity of the basic therapies and of other stored and/or programmable data functions are limited only by memory type and capacity in the cardiac stimulator and associated programming unit.

Figure 2A:
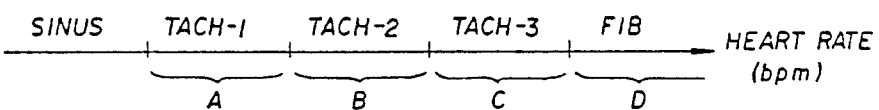
FIGS. 2a and 2b are diagrams illustrating the assignment (prescription) of exemplary therapy regimens to the arrhythmia classes.
Figure 2B:
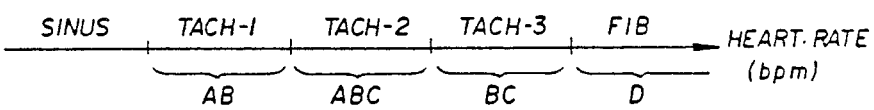

In one exemplary embodiment of the Haluska et al application, the four basic therapies employed are A) nonaggressive pacing bursts, B) aggressive pacing bursts, C) cardioverting shocks, and D) defibrillating shocks. A particularly simple regimen assigns therapy A to TACH-1, B to TACH-2, C to TACH-3, and D to FIB, as shown in FIG. 2a. Preferably, however, the therapies are delivered in a sequence of increasing aggressiveness with increasing rate of the tachyrhythmia and/or with passage of time for a continuing tachyrhythmia. Referring to FIG. 2b, and using exemplary programmed fine structures for the selected therapies, on detecting a class TACH-1 VT, the device initially applies a single extra-stimulus pacing pulse as therapy A for ventricular stimulation. If the tachycardia continues it is sensed by a redetection algorithm on completion of delivery of therapy A. Thereupon, an autodecremental burst of pacing pulses is delivered as therapy B. Unless certain therapy control options are selected by the physician, as described in the Haluska et al application, the sequence A-B will be repeated while the VT remains in progress in class TACH-1, up to the device's capability for repetitions.

If the VT accelerates to class TACH-2, a default sequence of therapies programmed by the physician is instituted for that class (e.g., A-B-C), which follows the rule that on acceleration or deceleration of the arrhythmia, the therapy used for the old class is ceased and the least aggressive therapy prescribed for the new class is commenced immediately. If a sequence of therapies is programmed for the new class, the sequence is delivered in the order from least aggressive to more aggressive. If the VT had accelerated to TACH-3 during the therapy for TACH-1, the cardiac stimulator commences delivery of the therapy sequence set for TACH-3. In that instance, an autodecremental pacing burst (B) is delivered first, and if that fails to terminate the tachycardia, a 2-joule cardioverting shock (C) is applied. Upon termination of the arrhythmia, the therapy regimen is discontinued. For patients having a tendency to accelerate spontaneously from VT to VF, the therapy regimen programmed by the physician would generally be more aggressive than that for patients without such predisposition.

The partitioning of the heart rate spectrum into arrhythmia classes provides, in and of itself, a basis for an arrhythmia detection technique; however, it is desirable to develop additional information beyond the rate boundaries of these classes to more reliably classify the arrhythmia. For example, a single cardiac event might be detected in TACH-3 which could be attributable to an isolated premature ventricular contraction (PVC) —often observed in individuals without heart disease, and not the start of a reentrant VT. Moreover, a detection scheme based solely on rate ranges might fail to distinguish between a sinus VT and a reentrant VT because of the possible considerable overlap in rates. The cardiac stimulator of the Haluska application employs a reliable arrhythmia detection technique as follows.

Because reentrant tachycardias are typically characterized by an abrupt onset (in contradistinction to a gradual ramping up in exercise-induced sinus tachycardias) and a stable high rate (in contradistinction to the rate fluctuation of exercise tachycardias), the foundation of the arrhythmia detection system is four basic detection criteria, namely, 1) high rate (HR), 2) sudden onset (SO), 3) rate stability (RS), and 4) sustained high rate (SHR). The HR criterion is a high rate run length of n consecutive intervals at a heart rate exceeding a selected base rate, where n may range, for example, from 1 to 255 intervals (beats) at a rate exceeding the boundary rate separating the SINUS and TACH-1 classes. Thus, if n is programmed to be 6 and the lower boundary rate for TACH-1 is programmed to be 100 beats per minute (bpm), HR is satisfied if the patient's heart rate exceeds 100 bpm over the course of at least 6 consecutive beats.

The SO criterion consists of a physician-programmed step increase (delta change) in the heart rate, and is satisfied if the patient's heart rate suddenly jumps by an amount exceeding this delta.

The RS criterion consists of two physician-programmed factors, one being a run length of n consecutive intervals exceeding a selected base rate, and the other a specified rate stability delta. RS is satisfied if the patient's heart rate exceeds the specified base rate (which typically may be the minimum boundary rate for the TACH-1 region) over n consecutive beats, and that heart rate does not vary by more than the specified delta rate over those n consecutive beats.

The SHR criterion is analogous to HR except that the specified run lengths differ, SHR specifying a considerably longer run length n than that used for the HR criterion.

These four basic detection criteria are combined by Boolean logic into nine tachycardia detection algorithms, viz.,
1. high rate (HR);
2. high rate and sudden onset (HR and SO);
3. high rate and sudden onset, or sustained high rate ([HR and SO]or SHR);
4. high rate and rate stability (HR and RS);
5. high rate and rate stability, or sustained high rate ([HR and RS]or SHR);
6. high rate and sudden onset and rate stability (HR and SO and RS);
7. high rate and sudden onset and rate stability, or sustained high rate ([HR and SO and RS]or SHR);
8. high rate and either sudden onset or rate stability (HR and [SO or RS]);
9. high rate and either sudden onset or rate stability, or sustained high rate ( HR and [SO or RS]or SHR).

Algorithms containing SHR are utilized because it is possible that the other algorithms may specify criteria too stringent to allow the respective composite algorithm to be satisfied by a reentrant tachycardia; SHR acts as a "safety valve" to detect persistent high rate activity as a reentrant VT. For example, if a tachycardia is detected and HR is satisfied but SO and/or RS are not, satisfaction of SHR will trigger the selected therapy. Nevertheless, it has been found that a ventricular response to atrial fibrillation may be classified, incorrectly, as a reentrant VT by algorithm 7 above. The atrial fibrillation can result in a sustained high ventricular rate which deceives the SHR criterion, resulting in erroneous detection of a reentrant VT. According to the present invention, this problem is eliminated by adding an algorithm to the above list of tachycardia detection algorithms which will assure that ventricular response to atrial fibrillation alone is not detected as a reentrant VT. In particular, the ventricular response to AF does not evidence rate stability, so a tenth detection algorithm is provided:
10. high rate and sudden onset and rate stability, or sustained high rate and rate stability ([HR and SO and RS]or [SHR and RS]).

Figure 5:
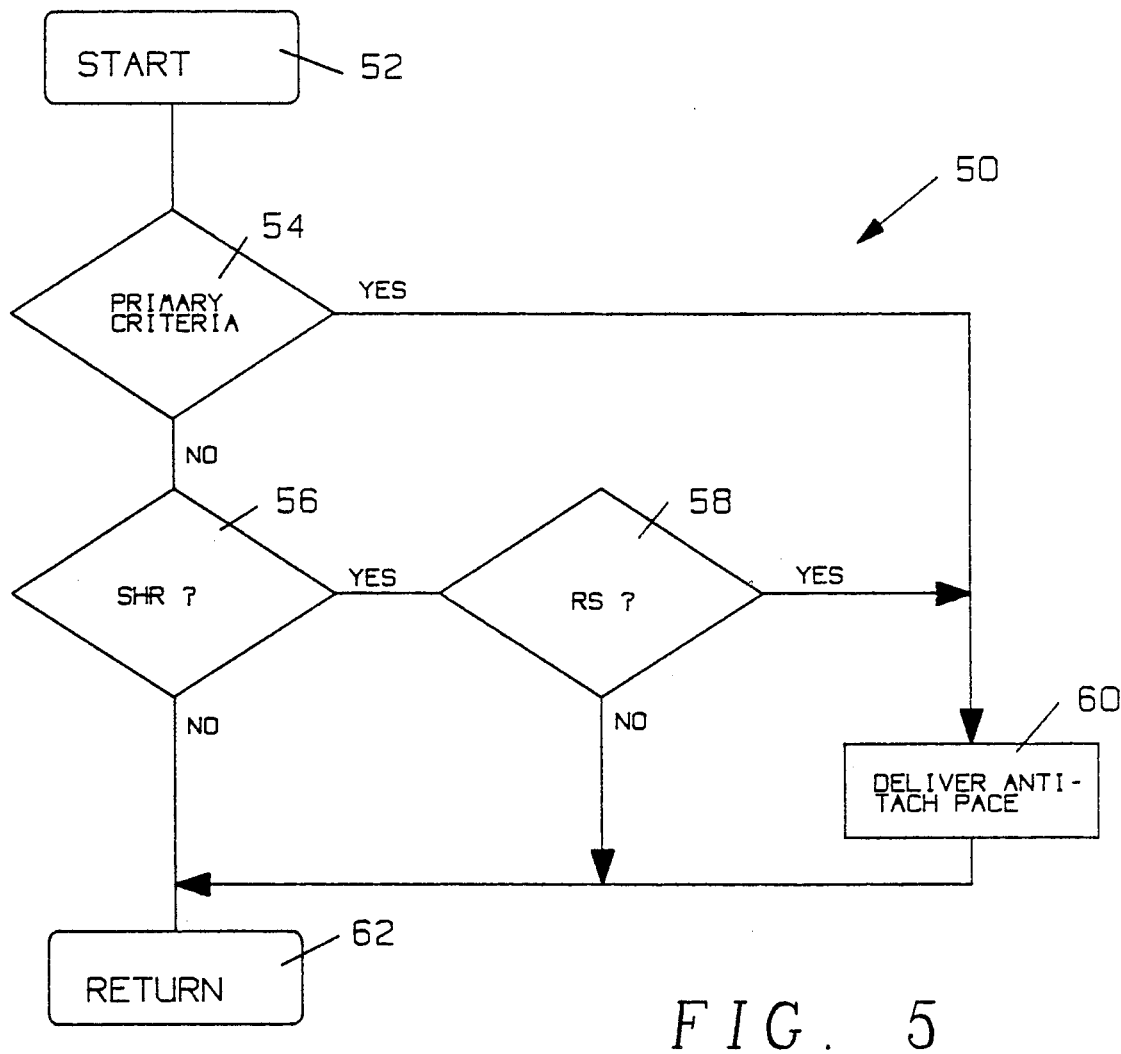
FIG. 5 is a flow chart of an arrythmia detection algorithm.

The preferred algorithm, generally designated 50, for assuring that ventricular response to atrial fibrillation alone is not detected as a reentrant VT is illustrated in FIG. 5. When the algorithm is invoked 52, the primary criteria for detecting pacemaker terminable tachycardia is implemented 54. In the preferred embodiment, this will most frequently comprise the detection of high rate and sudden on-set and rate stability. If these criteria are satisfied, an anti-tachycardia therapy should be delivered 60. If the primary criteria is not satisfied, sustained high rate should be tested 56. If sustained high rate is detected, an additional test should be implemented for rate stability 58. If both criteria, sustained high rate 56 and rate stability 58 are met, the anti-tachycardia therapy should be delivered 60. These subroutines can then be ended 62.

The arrhythmia detection algorithms are used for deciding that the detected evidence is sufficient to declare that a reentrant tachycardia is in progress. In essence, these algorithms serve to distinguish between arrhythmias which should be treated by the device and those which should not be treated. The detection technique applies the principle that the algorithm stringency should decrease with increasing rate and thus with increasing hemodynamic intolerance of the arrhythmia. In the preferred embodiment described in the co-pending Haluska et al application, the physician may specify three different detection algorithms, each for a different tachycardia class, the most stringent detection algorithm of those specified being assigned to the tachycardia class having the lowest rate range, and the progressively more relaxed detection algorithms being assigned to the successively higher rate range classes. Thus, if a highly stringent detection test applied to the TACH-1 region results in inconclusive evidence as to whether a reentrant tachycardia is in progress, and a moderately stringent test applied to the TACH-2 region is satisfied, the evidence is compelling that a reentrant VT is indeed in progress.

Figure 3A:
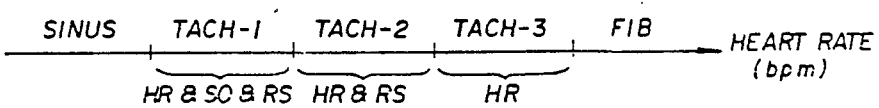
FIGS. 3a and 3b are diagrams illustrating the designation of detection criteria algorithms to the arrhythmia classes.

By way of example, FIG. 3a illustrates the selection of detection algorithnms for the tachycardia classes TACH-1, TACH-2, and TACH-3 of FIG. 1a. The most stringent of the algorithms depicted in FIG. 3a, HR and SO and RS, is assigned to the TACH-1 region; and the most relaxed test, HR is assigned to the TACH-3 region; and a moderate test intermediate the other two, HR and RS, suffices for the TACH-2 region.

The number of detection criteria is reduced for purposes of redetection following initial screening of the VT, because of the need to deliver the next therapy as quickly as possible if the VT is still in progress and also because less stringent detection criteria will provide suitable compelling evidence of the continuing VT. Any criterion which is no longer applicable is discarded from use in redetection. For example, the SO criterion is not viable after initial detection of a VT, so it is eliminated for purposes of redetection of the progress of that VT. Similarly, the SHR criterion is of no value for redetection, once having identified a VT in progress, so algorithms 2,3, and 5 through 10, inclusive, of the above list are eliminated for purposes of redetection.

HR (algorithm 1), and HR and RS (algorithm 4), are the only remaining tests suitable for redetection criteria. Each of HR and RS is useful in both initial screening and redetection, and each is assigned two separately programmable n's, namely ni (for initial detection) and nr (for redetection), because for HR a rather long run of consecutive high rate intervals (ni) may be deemed necessary for reliable initial detection of a VT but a relatively shorter run length (nr) will suffice for redetection, and similarly for RS, a shorter run of consecutive high rate intervals (nr) of relatively invariant rate is suitable for redetection compared to the run length (ni) used for the initial screening.

Figure 3B:
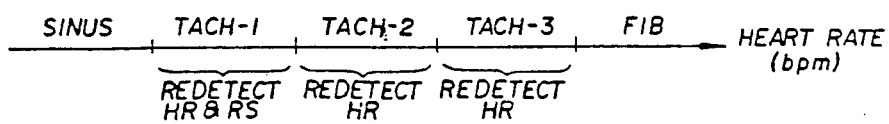

As with the initial screening algorithms, the physician may program a different redetection algorithm for each of the VT classes. In the scheme illustrated in FIG. 3b, the more stringent redetection algorithm HR and RS is assigned to class TACH-1, and the more relaxed redetection test HR is assigned to each of the TACH-2 and TACH-3 classes.

A different set of basic criteria is provided for purposes of detecting fibrillation, namely, fibrillation rate (FR) which is somewhat analogous to the HR criterion for tachycardia detection, but a run length of n consecutive intervals must occur at a heart rate exceeding the rate at the upper boundary of the highest VT region of the rate continuum for FR to be satisfied; and F x/y, which specifies that x fibrillation rate intervals must occur within y consecutive intervals. The latter criterion detects VF despite the characteristic erratic heart rate and widely variable signal amplitude. To insure that an erratic, high rate, hemodynamically compromising arrhythmia is rapidly detected, and to bias the detection in favor of VF and away from a TACH-3 VT, additional rules applied to the VT and VF detection criteria are described in detail in the co-pending Haluska et al application.

The two basic fibrillation detection criteria are combined by Boolean logic into three VF detection algorithms, viz.:
1. fibrillation rate (FR)
2. fibrillation x out of y (F x/y)
3. fibrillation rate or fibrillation x out of y (FR or F x/y)

After detection of an arrhythmia in one of the TACH or FIB classes, and in response, the delivery of the prescribed therapy sequence, the implanted stimulator assesses whether sinus rhythm has been reestablished in a manner described in the Haluska et al application.

Figure 4:
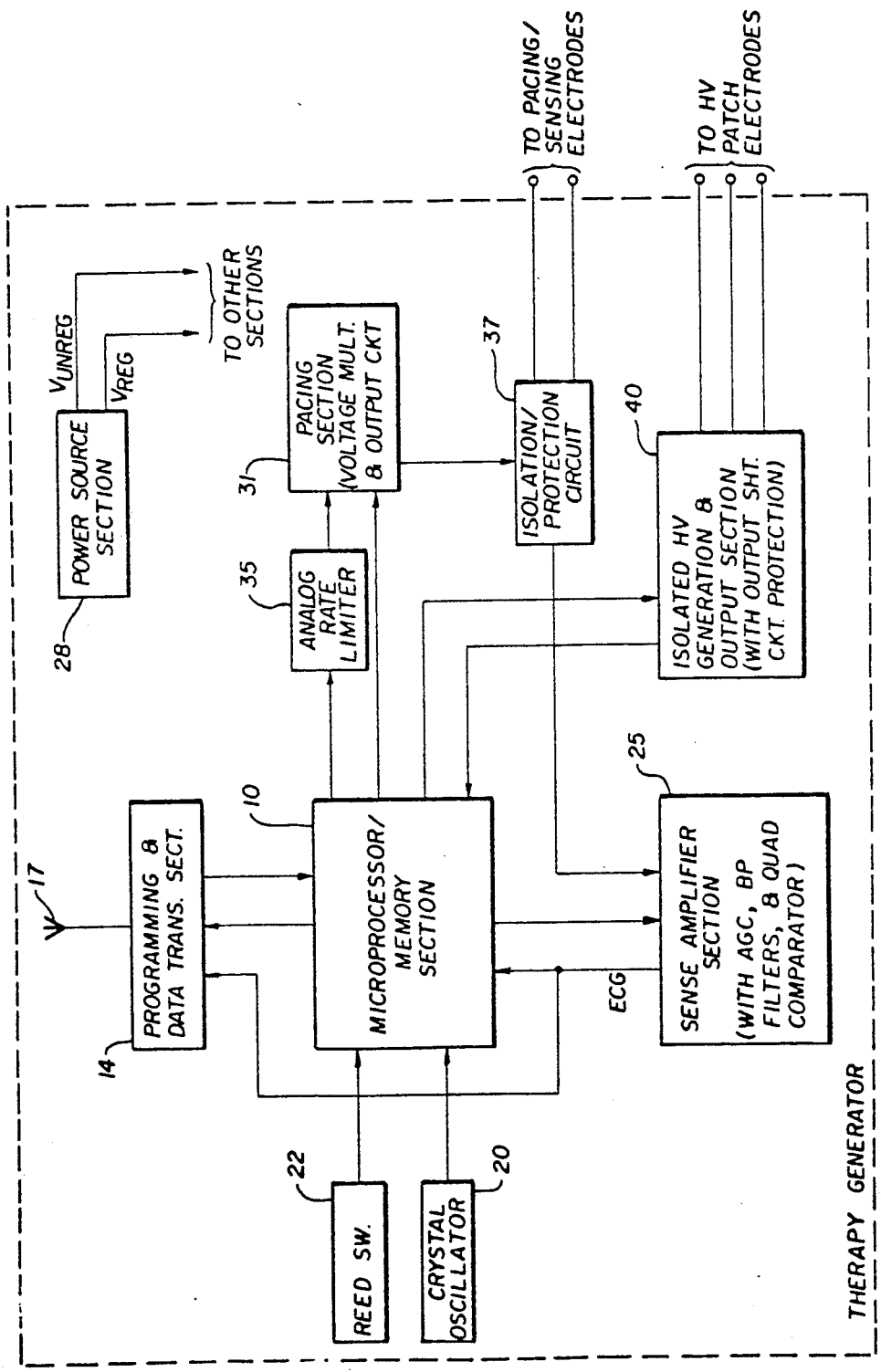
FIG. 4 is a block diagram of an implantable cardiac stimulator according to the Haluska et al application, in which the present invention may be employed.

The cardiac stimulator in which the present invention may be used is implantable and includes a therapy generator for detecting and distinguishing the significance of the patient's cardiac activity, and responsive to abnormal arrhythmias for generating and managing the delivery of pacing and shock therapies, and lead/electrode assemblies for sensing cardiac activity and for delivering the respective pacing and shock impulses to the patient's heart, each as described in detail in the Haluska et al application. Referring to FIG. 4, the therapy generator includes a section 10 comprising a central microprocessor with associated memory capacity including random access memory (RAM) and read only memory (ROM), for processing and storing the data necessary for the purposes described above. Section 10 is bidirectionally coupled to a programming and data transmission section 14 to transmit data to receiving and monitoring equipment for analysis and assessment of the cardiac functions of the patient and the operating condition of the implanted device, and for receiving program instructions and data from the external programmer, via an implanted antenna 17.

A crystal oscillator 20 electrically coupled to section 10 provides precise timing signals for system operation. Reed switch 22 is also electrically connected to section 10 to permit limited external control by the patient of programmable functions, if permitted by the physician, by using an external magnet to control actuation of the switch.

A sense amplifier section 25 including automatic gain control and bandpass filtering is coupled to section 10 for transmitting ECG signal information to the microprocessor and for receiving control signals from the microprocessor. The sense amplifier is also connected to data transmission section 14 so that the ECG telemetry signal information may be supplied via the latter to external monitoring equipment. A quad comparator within section 25 provides the link for converting the ECG sense signal information obtained from the sensing electrode(s) and processed by the sense amplifier into digital information suitable for use by the microprocessor. The microprocessor is within a feedback loop of the sense amplifier to provide improved automatic gain control. The sense amplifier enhances the ECG signals to aid the tracking of signal content of rapidly varying amplitude, such as fibrillation signals. In addition, bandpass filtering provides a dual function of (1) reducing the amplitude of signals outside the frequency band of interest and (2) further amplifying the low frequency (e.g., fibrillation) signals within that band in the absence of normal R-waves.

The power source section 28 of the overall stimulator system comprises high rate battery cells, a voltage regulator and a priority power sequencer. The voltage regulator circuit has a voltage divider to provide a 3:1 reduction if three cells are used in series, or a 2:1 reduction if only two cells are employed, to improve power source efficiency. The priority power sequencer assures adequate power is made available to essential circuit functions, e.g., the control logic, during periods when there would otherwise be high current drain on the cells, such as during charge up of the high voltage capacitors in preparation for the delivery the defibrillating or cardioverting shock therapies.

The pacing section 31 of the system includes a voltage multiplier and output section, the former serving to scale up the regulated supply voltage from power source section 28 by multiples of one, two or three. The output section provides the output switching from this scaled voltage to deliver the pacing stimuli to the patient,s heart via the pacemaker circuit including cathodic stimulating and anodic reference electrodes, under the control of the microprocessor.

An analog rate limit circuit 35 between microprocessor/memory section 10 and pacing section 31 is employed to controllably limit the pacing rate, to safeguard against pacemaker runaway in the event of failure of the crystal oscillator circuit, but the rate limiter is automatically disabled whenever an intentionally high rate of pacing pulses is required, such as during the generation of a burst pacing therapy.

The leads for the pacing and sensing electrodes are electrically monitored by isolation/protection section 37 to protect low voltage, low power components of the stimulator from the high voltage of the defibrillating shocks generated by the stimulator or applied from an external defibrillator that may be used on the patient during emergency medical procedures.

The cardioverter/defibrillator shock therapy portion of the stimulator includes an isolated high voltage generator and output section 40. The voltage generator circuitry includes a high voltage oscillator coupled via an isolation transformer to output capacitors for charging the capacitors to the required voltage levels for the cardioverting and defibrillating shocking pulses, under the control of the microprocessor.

A low power analog-to-digital (A/D) converter in section 40 is utilized to monitor the voltage on the capacitors, to permit the microprocessor to set the desired high voltage output level in accordance with the physician-programmed fine structure energy content of the applicable shock therapy. Monitoring of the capacitor voltage also allows the microprocessor to measure the residual charge on the capacitors after delivery of each output pulse, and thereby to estimate the amount of energy consumed in the delivery for ongoing assessment of remaining capacity of the battery cells. In addition, the A/D converter input circuit may be switched by the microprocessor for connection to the power source section 28 to monitor the battery voltage, and thereby determine the present condition of the cells.

Output section 40 also contains level shifters and isolation transformers to convert the microprocessor-supplied low level logic control signals to the control signal levels required to drive the output switches of that section. The output switches themselves are of low "on" impedance and capable of handling the high voltages and currents being generated, to control the delivery and polarity of each output pulse. A short circuit protection circuit is provided in output section 40 to open the output circuit in the event that the current through that circuit rises above a predetermined level, thereby preventing discharge of the capacitors into a very low impedance —such as if the defibrillator patch electrodes were shorted— and protecting the output switches from overstress and potential destruction.

Although a presently preferred embodiment of the invention has been described herein, it will be apparent to the reader skilled in the field to which the invention pertains, that variations and modifications of the described embodiment may be made without departing from the true spirit and scope of the invention. Accordingly, it is intended that the invention be limited only to the extent required by the appended claims.

What is claimed is:

1. A cardiac stimulator for detecting and treating ventricular tachyrhymias comprising:
    means for detecting events in a heart of a patient;
    means for identifying a selected high rate of said detected events;
    means for identifying a selected sudden onset of said detected events;
    means for identifying a selected rate stability of said detected events;
    means for identifying a selected sustained high rate of detected events;
    means for delivering a selected therapy to the heart responsive to either a first output from at least two said means, the sudden onset identifying means, or the rate stability identifying means or a second output from both the sustained high rate identifying means and the rate stability identifying means.

2. The cardiac stimulator according to claim 1 wherein the first output comprises output from the high rate identifying means and from the sudden onset identifying means.

3. The cardiac stimulator according to claim 2 wherein the first output also includes output from the rate stability identifying means.

4. The cardiac stimulator according to claim 1 wherein the first output comprises output from the high rate identifying means and from the rate stability identifying means.

5. The cardiac stimulator according to claim 1 wherein the first output comprises output from the high rate identifying means and at least one output from either the rate stability identifying means or the sudden onset identifying means.

6. A method for detecting and treating ventricular tachyrhythmias comprising:
    detecting events in a heart of a patient;
    identifying a selected high rate of said detected events;
    identifying a selected sudden onset of said detected events;
    identifying a selected rate stability of said detected events;
    identifying a selected sustained high rate of detected events;
    delivering a selected therapy to the heart based on either identifying at least two criteria from a selected group of high rate, the sudden onset, and said rate stability or identifying both sustained said high rate and rate stability.

7. The method according to claim 6 wherein the criteria identifying step comprises identifying said high rate and said sudden onset.

8. The method according to claim 7 wherein the criteria identifying step also includes identifying rate stability.

9. The method according to claim 6 wherein the criteria identifying step comprises identifying high rate and rate stability.

10. The method according to claim 6 wherein the criteria identifying step comprises identifying said high rate and either said rate stability or sudden onset.

* * * * *